United States Patent [19]
Jones

[11] Patent Number: 5,564,416
[45] Date of Patent: Oct. 15, 1996

[54] VENTILATORS FOR PROMOTING LUNG FUNCTION

[75] Inventor: Norman S. Jones, Leighton Buzzard, England

[73] Assignee: pneuPAC Limited, Bedfordshire, England

[21] Appl. No.: 315,536

[22] Filed: Sep. 30, 1994

[30] Foreign Application Priority Data

Oct. 6, 1993 [GB] United Kingdom ................. 9320619

[51] Int. Cl.⁶ .................................................. A61M 16/00
[52] U.S. Cl. .............................. 128/204.21; 128/204.18; 128/205.25
[58] Field of Search ...................... 128/204.18, 205.18, 128/205.24, 204.21, 204.24, 204.25, 205.25

[56] References Cited

U.S. PATENT DOCUMENTS

| | | | |
|---|---|---|---|
| Re. 29,778 | 9/1978 | Stewart | 128/204.18 |
| 3,669,108 | 6/1972 | Sundblom et al. | 128/204.26 |
| 3,881,480 | 5/1975 | Lafourcade | 128/204.18 |
| 3,916,889 | 11/1975 | Russell | 128/204.24 |
| 4,003,377 | 1/1977 | Dahl | 128/204.23 |
| 4,057,059 | 11/1977 | Reid, Jr. et al. | 128/204.24 |
| 4,227,523 | 10/1980 | Warnow et al. | 128/204.24 |
| 4,301,793 | 11/1981 | Thompson | 128/204.21 |
| 4,592,349 | 6/1986 | Bird | 128/204.25 |
| 4,922,962 | 5/1990 | Jones | 137/624.14 |
| 5,007,457 | 4/1991 | Jones | 137/624.14 |
| 5,241,955 | 9/1993 | Dearman et al. | 128/204.18 |

FOREIGN PATENT DOCUMENTS

| | | |
|---|---|---|
| 0097060 | 12/1983 | European Pat. Off. . |
| 0383069 | 8/1990 | European Pat. Off. . |
| 0342883 | 4/1992 | European Pat. Off. . |
| 0343818 | 4/1992 | European Pat. Off. . |
| 1530478 | 6/1968 | France . |
| 1533550 | 11/1978 | United Kingdom . |
| 9001965 | 3/1990 | WIPO . |
| 9217235 | 10/1992 | WIPO . |

OTHER PUBLICATIONS

Avian™ Transport Ventilator Brochure, L1255, dated Mar. 1993.
Ycon Depuis, "Ventilators: Theory and Clinical Application," St Louis: CV Mosby Co., 1986, pp. 225, 364–5.

Primary Examiner—Edgar S. Burr
Assistant Examiner—Eric P. Raciti
Attorney, Agent, or Firm—David V. Radack; Eckert Seamans Cherin & Mellott

[57] ABSTRACT

A ventilator for inducing or assisting lung function in humans is characterized by a control system that provides for semi-automatic operation in which a single complete ventilation cycle in accordance with predetermined ventilation parameters (tidal volume, durations of inhalation and exhalation phases) is initiated by operation of a trigger. The ventilator is particularly useful in one-man resuscitation by CPR. The control system may require a discrete trigger operation to initiate each successive ventilation cycle or it may provide for continuous operation with timed successive cycles, in the manner of an automatic ventilator, by holding or latching the trigger. Various embodiments based on gas-powered ventilators are disclosed but the invention is also applicable to electrically operated or controlled ventilators. In a typical embodiment (FIG. 1) the output line (6) of a pneumatic oscillator is controlled by a diaphragm (22) held closed by a spring (36) loaded by a trigger (31) that when operated relieves the spring load and permits the diaphragm to open the output line. The output line pressure then acts on the diaphragm to hold the output line open until output pressure falls at the termination of the inhalation cycle, whether or not the trigger is released before that instant.

23 Claims, 4 Drawing Sheets

VENTILATORS FOR PROMOTING LUNG FUNCTION

BACKGROUND OF THE INVENTION

1. Field of the Invention

This invention concerns ventilators for inducing or assisting lung function in human patients. The invention is especially concerned with ventilators for use in resuscitation, rescue breathing and patient transport.

2. Background Discussion and the Prior Art

Ventilators for such purposes have been available for many years and two main types are in widespread use today: automatic ventilators in which the lung ventilation parameters (tidal volume, phase durations) are determined by control settings of the ventilator; and manual ventilators in which the ventilation parameters are directly controlled by the user.

Automatic ventilators have the advantage that when once the control settings for required parameters have been established—in some cases once and for all during manufacture—efficient lung ventilation can be consistently maintained through repeated inhalation/exhalation cycles without intervention of the user. In manually controlled ventilators, the delivered tidal volume of breathable gas and the inhalation and exhalation times for each cycle are determined individually by action of the user, requiring continual attention and the exercise of judgement by the user.

Automatic ventilators offer unquestionable advantages for rescue breathing and patient transport but can have some disadvantages in one-man resuscitation in cases of cardiac arrest, wherein the common resuscitation technique (cardiac pulmonary resuscitation, CPR) involves applying a sequence of chest compressions interrupted at regular intervals by one or more lung ventilations: typically two lung ventilation cycles followed by 15 chest compressions followed by two further lung ventilation cycles, and so on. With an automatic ventilator continuously delivering a train of pulses of breathable gas to a face mask at a constant rate, this resuscitation technique demands that the face mask be applied to the patient for two ventilation cycles and then removed; the required number of chest compressions be then applied; and thereafter the face mask be reapplied to the patient: all in synchronism with the operation of the ventilator so that this delivers a breathable gas pulse immediately the mask has been applied or re-applied to the patient. Especially in the case of one-man resuscitation, this requires dexterity and skill on the part of the rescuer to achieve the required synchronisation of the manual operations with the cyclic operation of the ventilator and therefore many rescuers opt to use a manual ventilator in such circumstances; the manual ventilator allows the rescuer to initiate delivery of a breathable gas pulse when required to fit in with the sequence of chest compressions and mask application.

A need can therefore be perceived for a rescue/resuscitation ventilator that can be more conveniently used in CPR than existing ventilators, by having the ability to deliver instantly on demand a single controlled ventilation cycle of predetermined tidal volume and duration, so avoiding the synchronisation requirements of the automatic ventilator and also the disadvantages inherent in the use of existing manual ventilators.

There have already been proposals for ventilators that are switchable between an automatic mode of operation and a fully manually controlled mode. However, in the manually controlled mode, these ventilators exhibit the above discussed disadvantages of manually controlled ventilators and, thus, cannot offer a satisfactory solution to the problem.

SUMMARY OF THE INVENTION

In accordance with the present invention, a ventilator is characterised by a control system providing a semi-automatic mode of operation in which a complete ventilation cycle in accordance with predetermined ventilation parameters may be initiated by trigger operation. The control system may require a discrete trigger operation to initiate each of a succession of ventilation cycles or it may provide for sustained operation of the trigger to cause continued operation of the ventilator in the manner of an automatic ventilator: latching or functionally equivalent means may provide for continuous operation of the ventilator in the manner of an automatic ventilator, without user intervention.

The invention may be implemented in ventilators in which functional control of the ventilation cycle is exercised by an electrically operated or controlled mechanism. However, because of the many advantages offered by gas-powered ventilators, the invention is preferably implemented in a gas-powered ventilator in which timing and control functions are provided by pneumatic mechanisms. The invention will accordingly be further discussed and described in respect of such an implementation.

Thus, the invention is preferably implemented in a gas-powered ventilator the output of which is controlled by a pneumatic oscillator. This may take any of a variety of forms and may, for instance, be as disclosed in British Patent 1,533,550 or be of the construction in which a piston (or its equivalent, e.g. a diaphragm) is reciprocable to open and close a flow path between a source of pressurised breathable gas and a gas pulse output: examples of such an oscillator are disclosed in French Patent 1,530,478 and U.S. Pat. No. 3,881,480. A pneumatic oscillator of such construction desirably incorporates the inventions disclosed in U.S. Pat. No. 4,922,962 and European Patent 0,342,883, and in U.S. Pat. No. 5,007,457 and European Patent 0,343,818.

DESCRIPTION OF EMBODIMENTS

Each illustrated embodiment incorporates a pneumatic oscillator that in these embodiments comprises a piston 1 reciprocable in a cylinder 2 and biased by a spring 3 towards the right as seen in the drawing, to cause an annular sealing lip 4 on the piston to engage a resilient seal surrounding a port 5 in the end of the cylinder 2. In the arrangement shown, the port 5 constitutes an outlet port connected to output line 7 by way of an outlet branch 6 and a restrictor 8. The outlet branch 6 also connects with a feedback line 9 through a restrictor 10, the feedback line 9 connecting with the end of the cylinder 2 opposite to that containing the port 5.

A port 11 at the righthand end of the cylinder 2 and outboard of the port 5 serves for the admission of pressurised breathable gas, for instance compressed air or oxygen, to this end of the cylinder 2 from a source shown symbolically at 12.

In a typical known automatic ventilator incorporating a pneumatic oscillator of the form just described, the outlet branch 6 connects directly with the port 5 of the cylinder 2 and to understand the following description of the operation of the oscillator, such a direct connection should be assumed.

The drawing shows the piston 1 in a flow path-closing position in which the sealing lip 4 engages the seal surrounding port 5. With the piston in this position, breathable gas from the source 12 entering the port 11 is isolated from the port 5. However, source gas pressure acting on the annular area of the piston outboard of the sealing lip 5 is sufficient to overcome the thrust of spring 3 and to drive the piston to the left as seen in the drawings. This movement of the piston takes place, as described below, with a snap-action, connecting the port 11 to the port 5 and thence to the outlet branch 6, so enabling the gas to flow via the restrictor 8 to the output line 7 and also, via the restrictor 10, to the feedback line 9. As a consequence of the flow of gas through the feedback line to the lefthand end of the cylinder 2, at a rate controlled by the restrictor 10, pressure builds up in the cylinder to act on the piston 1 to supplement the force of the spring 3. Eventually the combined effects of the gas pressure and spring 3 cause the piston to move to the right as seen in the drawing, to return the piston to the illustrated position with the sealing lip 4 engaging the seal surrounding the port 5.

As the piston approaches its illustrated righthand end position, flow to the outlet branch 6 is restricted and the pressure therein drops so that there is a sudden shift in the balance of forces on the piston 1 and this completes its movement to the right with a snap-action to cut off flow to the port 5 and the outlet branch 6.

Pressure in the lefthand end of the cylinder 2 then decays by reverse flow through the feedback line and restrictors 10 and 8. When the gas pressure in the left hand end of the cylinder 2 has decayed to an appropriate extent, source gas pressure acting on the annular area of piston 1 outboard of the sealing lip 4 once again overcomes the force of the spring 3 and causes the piston 1 to commence to move towards the left as seen in the drawing. As it does so, it re-opens the pathway to the port 5 as above described and gas flows into the outlet branch 6, building up pressure therein which acts on the central area of the piston 1 to supplement the thrust of the source pressure on the outboard annular area of the piston. There is in consequence an abrupt change in the balance of forces acting on the piston 1 which moves with a snap-action to its lefthand end position. The described cycle repeats with a frequency determined by the relationship between the annular area outboard of the sealing lip and the total cylinder area, the bias force supplied by the spring 3 and the characteristics of the restrictors 8 and 10.

The principles of the operation of this form of pneumatic oscillator may be embodied in various arrangements in practical devices. For instance the restrictor 10 may be replaced by various restrictor/non return valve networks to achieve particular cycling patterns in the output line and to provide different operator control possibilities. The biasing of the piston may be achieved by means other than a spring: for instance the piston may have different areas effective at its opposite ends so that when both ends of the piston are exposed to equivalent pressures it experiences a net thrust towards the flow path-closing position. Whereas in the arrangement shown the port 5 constitutes an outlet port and the port 11 constitutes an inlet, the converse arrangement is possible. Moreover, the sealing lip 4 may be arranged on the end of the cylinder around the port 5 and co-act with a resilient facing on the end of the piston.

In accordance with the invention the oscillator is associated with a control system that provides for operation of the oscillator in a semi-automatic mode in which it performs individual cycles of operation in response to trigger action.

Thus, in the illustrated embodiments of the invention, the connection between the outlet branch 6 and the port 5 in the oscillator configuration is modified by inclusion of a valve arrangement 20 comprising a chamber 21 having a diaphragm 22 forming one wall thereof and movable to engage a sealing lip 23 surrounding an inlet port 24 that is connected to the port 5 of the cylinder 2. Outboard of the sealing lip 23 the chamber 21 has a connection 25 to the outlet branch 6. In practical embodiments the chamber 21 may be formed directly on the righthand end of the cylinder 2 so that port 24 is integrated with port 5. Alternatively, the valve arrangement 20 may be remote from the cylinder 2, its location being determined by the need for convenient operation of the trigger mechanism, described below, by the user of the ventilator.

Valve arrangement 20 provides a means for enabling and disabling the pneumatic oscillator without affecting any of its connections or the settings of the controls—such as restrictors 8 and 10—that determine its performance parameters. Thus, when diaphragm 22 is engaged with sealing lip 23 to isolate port 24 from port 25 and thus interrupt the connection between port 5 and the outlet branch 6, source pressure at port 11 of cylinder 2 is effective only to drive the piston 1 back to its lefthand end position in cylinder 2, but not to cause a flow of breathable gas to output line 7. However, when diaphragm 22 is clear of sealing lip 23, outlet branch 6 is effectively connected to port 5 so that oscillator action proceeds in the manner described, delivering to output line 7 breathable gas pulses of predetermined volume at intervals determined by the control settings of the oscillator.

The valve arrangement 20 is controlled by a trigger mechanism 30 comprising a trigger lever 31 pivoted at 32 and subject to the thrust of a bias spring 33 tending to rotate the lever 31 to engage its end 34 with a stop 35. A spring 36 acts between lever 31 and diaphragm 22, urging diaphragm 22 towards contact with sealing lip 23 to interrupt communication between port 5 and outlet branch 6, to inhibit operation of the oscillator in the manner described.

The arrangement is such that spring 33 is capable of holding the end 34 of lever 31 engaged with stop 35, for any position of the diaphragm 22, overpowering spring 36 as required. In this position of the lever 31, spring 36 is capable of holding diaphragm 22 in sealing engagement with sealing lip 23 against the thrust of source gas pressure acting only on the diaphragm area within the sealing lip 23, but not against source gas pressure acting on the full area of the diaphragm.

Thus, with the trigger lever 31 released and engaged with stop 35, and diaphragm 22 engaged with sealing lip 23, the oscillator action is held arrested with the piston 1 in its lefthand end position. However, rocking of trigger lever 31 in a clockwise direction about its pivot 32 as seen in the drawing and against the action of spring 33 relaxes the thrust of spring 36 upon diaphragm 22 and so enables the latter to lift clear of the sealing lip 23. Gas immediately then flows from source 12 via ports 11 and 5 of cylinder 2 and port 24 into the chamber 21, the pressure of this gas then acting on the full area of diaphragm 22 to hold the latter clear of sealing lip 23 for so long as source pressure is maintained at port 24 and whether or not trigger lever 31 is released and moves under the influence of spring 33 to re-engage its end 34 with stop 35. That is to say, the source pressure acting on the full area of diaphragm 22 is sufficient to overcome the thrust of spring 36 whatever the position of trigger lever 31.

It will accordingly be understood that if trigger lever 31 is momentarily depressed to relieve the thrust of spring 36 on diaphragm 22, a single full oscillator cycle will ensue with output of breathable gas at source pressure to outlet branch 6 until piston 1 moves to the right as seen in the drawing to interrupt communication between ports 11 and 5 of cylinder 2 in the manner described. At this point in the oscillator cycle, gas pressure in chamber 21 and outlet branch 6 commences to diminish and the thrust of spring 36 eventually moves diaphragm 22 into sealing engagement with sealing lip 23 to isolate port 5 from outlet branch 6. The oscillator cycle terminates when source gas pressure acting on piston 1 has restored the latter to its lefthand end position in cylinder 2.

Figure 1:
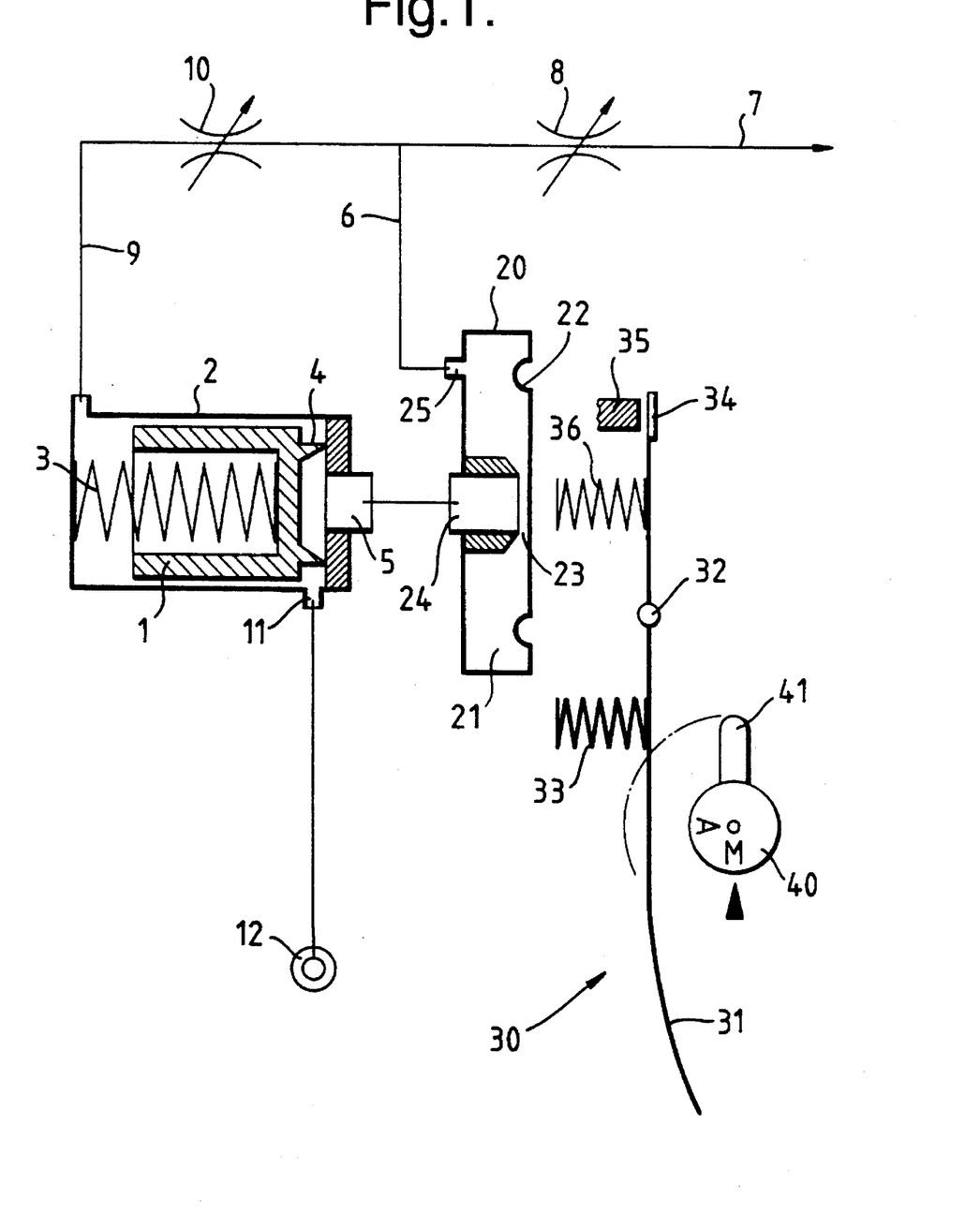
FIG. 1 is a schematic diagram of a pneumatic oscillator in accordance with the invention.

In the embodiment of FIG. 1, if trigger lever 31 is held depressed so that spring 36 is unable to force diaphragm 22 into sealing engagement with sealing lip 23, oscillator action will continue, so as to deliver breathing gas pulses to output line 7 in the manner of automatic ventilator, for so long as trigger lever 31 is held. When lever 31 is eventually released, oscillator action terminates with completion of the cycle then in progress, and restoration of piston 1 to its lefthand end position ready to commence a further cycle or series of cycles whenever the trigger lever 31 is again depressed.

The embodiment of FIG. 1 includes latching means in the form of a switch knob 40 having a cam or projection 41 that can be rotated from the position shown, in which projection 41 is clear of trigger lever 31, to a position in which projection 41 engages and holds trigger lever 31 in its depressed position against the action of spring 33, to provide for continuous fully automatic operation of the ventilator through continuous operation of the oscillator in the manner described, without manual intervention by the user.

It will accordingly be understood that by setting knob 40 in the position shown, a single operating cycle of the ventilator may be initiated, with instantaneous output of breathing gas, by brief depression of the trigger lever 31. The delivered tidal volume and the duration of the ventilation cycle will be determined by the ventilation parameters applicable to automatic operation: these are unaffected by the duration of depression of the trigger lever, provided that such duration is less than the period of one ventilation cycle.

Moreover, for so long as the trigger lever 31 is held depressed, the ventilator will continue fully automatic operation: this can result from the trigger lever being held depressed manually by the user or by appropriate setting of the knob 40.

The function of the latching means constituted by the knob 40 with its cam or projection 41 is to maintain open the connection between port 5 and outlet branch 6. This function can of course be achieved by other means, for instance a stop valve in a bypass connecting port 5 with branch 6.

Figure 2:
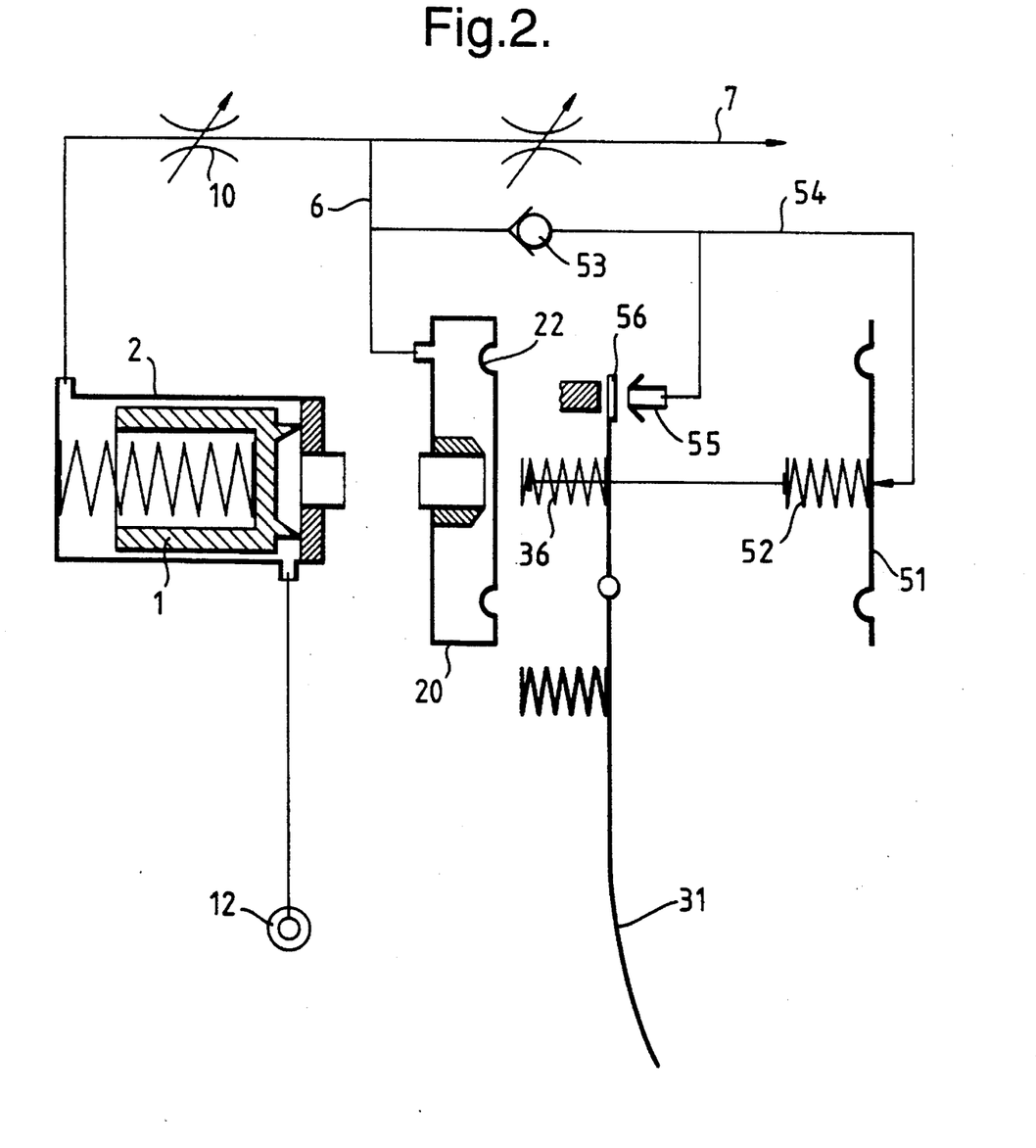
FIG. 2 is a schematic diagram of another embodiment of a pneumatic oscillator in accordance with another aspect of the invention.

The embodiment illustrated in FIG. 2 differs functionally from that of FIG. 1 in that depression of the trigger lever 31 is effective to release only a single cycle of operation by the oscillator. Thus, in this embodiment, the knob 40 is omitted because continuous depression of the lever 31 is ineffective to cause continuous automatic operation of the ventilator.

The embodiment of FIG. 2 is characterised by a diaphragm 51 that acts through a spring 52 on the diaphragm 22 to supplement the action of spring 36. Diaphragm 51 bounds a chamber (not shown) that is connected to outlet branch 6 via a non-return valve 53 and a line 54 that is also connected to a release orifice 55 that is obturated by a pad 56 on trigger lever 31 when the latter is depressed.

Thus, in the embodiment of FIG. 2, when trigger lever 31 is depressed and held to relieve the thrust of spring 36 on diaphragm 22, the latter lifts clear of the sealing lip 23 to establish communication between the cylinder port 5 and the outlet branch 6 in the manner described in relation to FIG. 1. As in the arrangement of FIG. 1, while the source gas pressure is thus applied to the full area of diaphragm 22 it is effective to hold this clear of sealing lip 23 for the duration of the required delivery of a gas pulse to output line 7, overpowering spring 36 should trigger lever 31 happen to be released during this period. However, in the arrangement of FIG. 2, when communication is established as described between port 5 and outlet branch 6, source gas pressure is also concurrently applied to diaphragm 51 thereby to increase the thrust of spring 52 upon diaphragm 22. This increased thrust of spring 52, by itself or in conjunction with the thrust of spring 36 with lever 31 released, is incapable of forcing diaphragm 22 into sealing engagement with sealing lip 23 until source gas pressure is cut off by the piston 1 moving to its righthand end position in cylinder 2: however, the thrust of spring 52 is sufficient to move diaphragm 22 into sealing engagement with the sealing lip 23 when source gas pressure is so cut off from the port 24 by action of piston 1, and pressure accordingly declines in chamber 21. Thus, should the trigger lever 31 be held depressed when piston 1 terminates a gas pulse, so that spring 36 is ineffective then to terminate the operation of the oscillator, the thrust of spring 52 on diaphragm 22 performs this function of arresting operation of the oscillator. The non-return valve 53 traps source pressure behind diaphragm 51 until such time as trigger lever 31 is released to enable spring 33 to rock pad 56 clear of the release orifice 55.

A ventilator having its valve arrangement 20 controlled in the manner illustrated in FIG. 2 is thus not capable of continued automatic operation by holding its trigger lever 31 depressed. Automatic operation, if required, must accordingly be obtained by alternative latching means such as a stop valve (not shown) in a bypass for valve arrangement 20, or a stop valve in the connection between outlet branch 6 and line 54. In the case of the latter arrangement, the means for operating the stop valve would conveniently include means for holding trigger lever 31 depressed for fully automatic operation.

Figure 3:
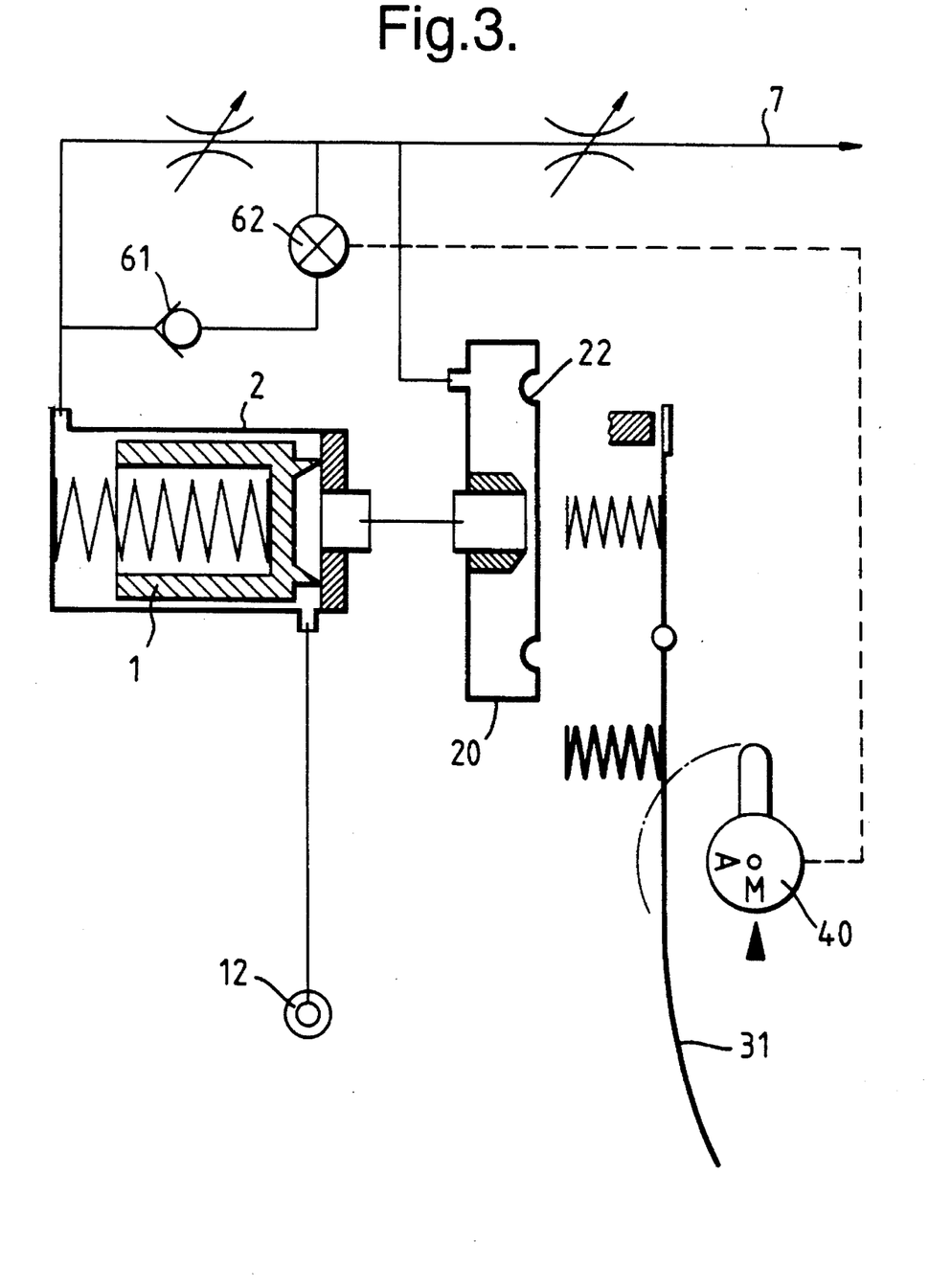
FIG. 3 is a schematic diagram of yet another embodiment of a pneumatic oscillator in accordance with yet another aspect of the invention.

FIG. 3 illustrates a modification of the arrangement of FIG. 1, in which the restrictor 10 is bypassed by a non-return valve 61 and a stop valve 62 so linked to the knob 40 as to be opened when this is set for manual (semi-automatic) operation. By this means the exhalation phase duration is reduced during semi-automatic operation of the ventilator under control of the trigger lever 31 and ensures that the piston 1 is rapidly returned to its lefthand end position in cylinder 2 following termination of the delivery of a breathing gas pulse initiated by a depression of the trigger lever 31. In this way the oscillator is rapidly "primed" to be able to deliver another full-volume breathable gas pulse immediately upon depression of the trigger lever 31. This facility can be advantageous in enabling another ventilation cycle to be initiated during CPR should the chest compression sequence be terminated earlier than the end of a "normal" exhalation phase duration.

Figure 4:
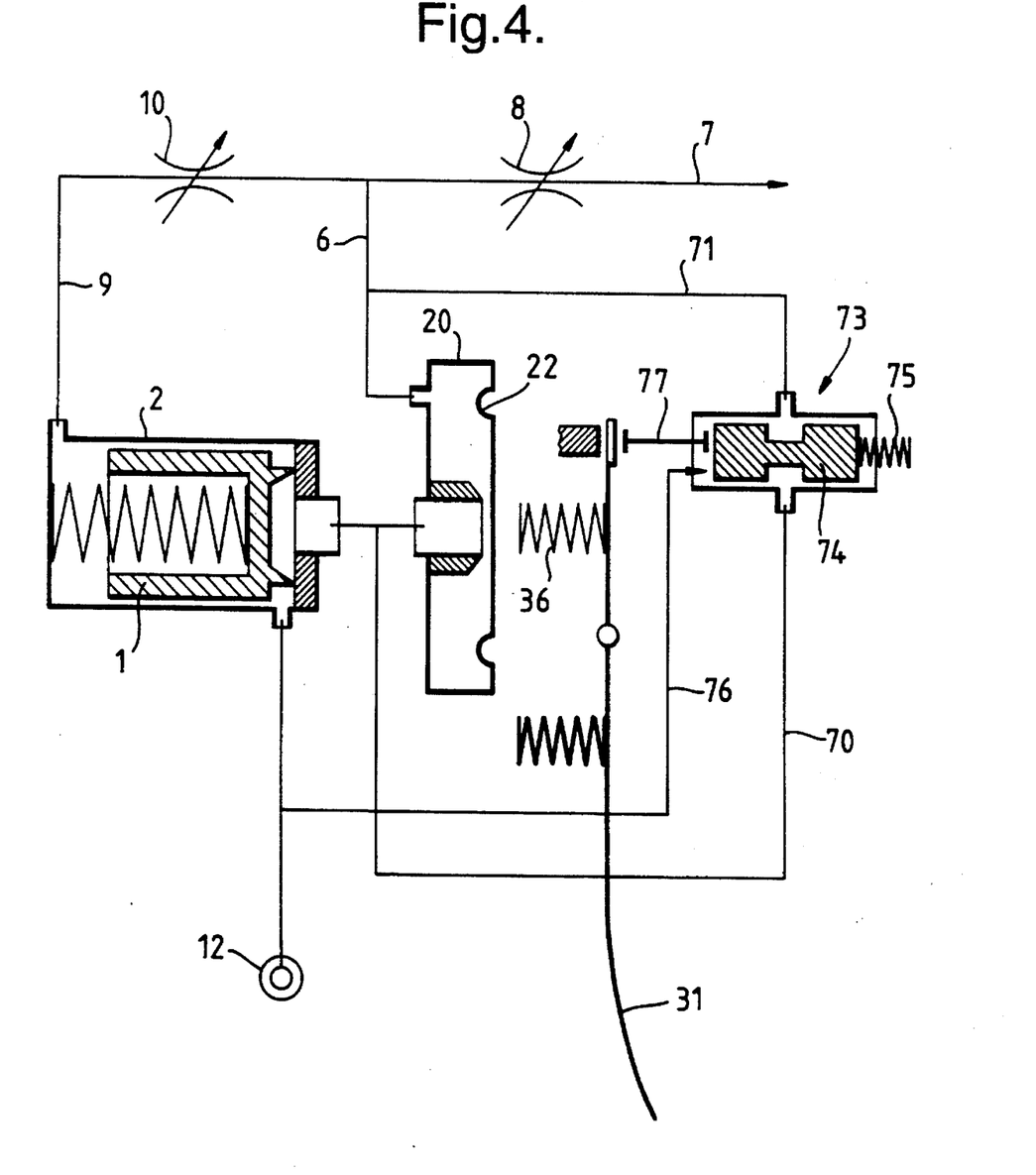
FIG. 4 is a schematic diagram of still yet another embodiment of a pneumatic oscillator in accordance with still yet another embodiment of the invention.

The embodiment illustrated in FIG. 4 provides for operation of the ventilator in a fully automatic mode at start-up, unless the semi-automatic mode is deliberately selected at that time. In this embodiment a bypass circuit comprising lines 70 and 71 respectively connected to port 5 and outlet branch 6 bridges the valve arrangement 20 to disable the function thereof to provide fully automatic operation of the ventilator when this is required. The bypass includes a valve 73 comprising a shuttle 74 biassed by a spring 75 towards the position in which it opens the bypass to enable fully automatic operation. The shuttle 74 is also subject to the pressure of source gas supplied from source 12 over line 76 and the arrangement is such that normal source gas pressure produces a thrust on the shuttle that balances the thrust due to spring 75.

Shuttle 74 of valve 73 is also mechanically connected to trigger lever 31 by the connection indicated schematically at 77, so that depression of trigger lever 31 to obtain semi-automatic operation of the ventilator is effective to displace shuttle 74 to the position in which it interrupts the bypass connection between lines 70 and 71, so making valve arrangement 20 effective to control the oscillator.

It will be understood that when the supply of breathable gas from source 12 is interrupted, spring 75 shifts shuttle 74 into the position to open the bypass constituted by lines 70 and 71. Accordingly, upon restoration of source gas pressure the bypass remains open and the ventilator commences operation in its fully automatic mode. However, the first depression of trigger lever 31 shifts the shuttle 74 to the position in which the connection between lines 70 and 71 is interrupted, the shuttle being held in this position thereafter so long as source gas pressure is available over line 76 to balance the thrust of spring 75. The valve arrangement 20 thus becomes effective to control semi-automatic operation of the ventilator, under control of trigger lever 31 in the manner described in relation to FIG. 1. Means, such as the knob 40 and projection 41 of FIG. 1 may be provided to hold trigger lever 31 depressed for maintained automatic operation after a period of semi-automatic operation.

A ventilator in accordance with the invention may incorporate all the usual facilities of lung ventilators. For instance, the breathable gas output by the ventilator may be supplied to any desired patient interface device: e.g. face mask or intra-tracheal tube, via an appropriate patient valve if required to provide for exhalation without the need for mask or tube removal, and the ventilator or the patient interface device may incorporate air mix facilities for diluting an oxygen source gas with air as and when required. Thus, for instance a gas-powered ventilator in accordance with the invention may be arranged to deliver oxygen from a suitable source to a patient valve including an entrainment mixer arranged in the manner disclosed in British Patent 2,174,609. The ventilator may also include a demand valve to permit spontaneous breathing by the patient to inhibit ventilator operation, for instance as disclosed in U.S. Pat. No. 5,016,626 and European Patent 0,343,824.

The functional components of a ventilator in accordance with the invention can be variously arranged to suit operational requirements. For example, the functional components may be arranged in a control unit connected by suitable ducting to a patient interface device or some or all of the functional components may be integrated with a patient interface device such as a face mask for convenient one-man operation.

As previously noted, the trigger mechanism is desirably arranged to be conveniently accessible to the user. This may be accomplished by incorporating the trigger mechanism and associated valve arrangement in the patient interface device but an alternative possibility is to arrange the trigger mechanism in a separate control unit and in a form in which it could be operated by the knee, foot or elbow of the user at a distance from the patient interface device.

While the invention has been described in respect of its preferred embodiments that involve gas-powered ventilators incorporating a pneumatic oscillator, it should be understood, as has been noted above, that the concept of the invention may be implemented in ventilators of other types and, especially, in ventilators in which functional control is exercised by electrical means.

I claim:

1. A lung ventilator comprising means for connection to a source of compressed breathable gas, an assembly for application to a patient for communication with the patient's respiratory system, a control system for controlling the supply of breathable gas from such source to a patient via said assembly, said ventilator including a manually operable trigger mechanism incorporated in said assembly, said control system providing a semi-automatic mode of operation in which, in response to activation of said trigger mechanism, a complete ventilation cycle in accordance with predetermined ventilation parameters is initiated, said control system including means to ensure that said cycle proceeds to completion regardless of any operation or release of said trigger mechanism after the movement which initiated said cycle and before its completion.

2. A lung ventilator according to claim 1, in which said assembly is a face mask assembly.

3. A lung ventilator according to claim 1, in which said assembly is an intra-tracheal tube.

4. A lung ventilator according to claim 1, including means for causing continued operation of said ventilator in the manner of an automatic ventilator.

5. A lung ventilator according to claim 1, in which said ventilator is gas-powered with timing and control functions provided by pneumatic mechanisms.

6. A lung ventilator according to claim 1, in which said control system provides means for sustained operation of said trigger mechanism to cause continued operation of said ventilator in the manner of an automatic ventilator.

7. A lung ventilator according to claim 6, in which said sustained operation means is a latching means providing for continuous operation of said ventilator, in the manner of an automatic ventilator, without user intervention.

8. A lung ventilator according to claim 7, further including means for adjusting the exhalation phase duration in said ventilation cycle in accordance with the setting of said latching means.

9. A lung ventilator according to claim 1, said ventilator including an outlet branch communicating with said assembly, said ventilator further comprising a pneumatic oscillator and a valve arrangement controlling a flow path for breathable gas from said source of compressed breathable gas via said oscillator to said outlet branch, said trigger mechanism being operable to open said flowpath and said valve arrangement being responsive to gas pressure in said outlet branch to maintain said flowpath open while breathable gas is output by said oscillator.

10. A lung ventilator according to claim 9, in which said valve arrangement comprises a chamber having an inlet port connected to said oscillator, a wall movable to close said inlet port and an outlet port connected to said outlet branch;

resilient means acting on said wall to urge said resilient means towards its inlet-port-closing position, said trigger mechanism being operable to relieve the action of said resilient means thereby to permit said wall to move to open said inlet port in response to gas pressure thereat, the arrangement being such that gas pressure in said chamber resulting from opening of said inlet port is effective to maintain said wall in an inlet-port-opening position despite the action of said resilient means.

11. A lung ventilator according to claim 10, including shut-off means responsive to gas pressure in said outlet branch to urge said chamber wall towards its inlet-port-closing position, and valve means for maintaining gas pressure effective on said shut-off means while said trigger mechanism is relieving the action of said resilient means.

12. A lung ventilator according to claim 10, including latching means for holding said trigger mechanism in a position to relieve the action of said resilient means and thereby to enable continuous automatic operation of said ventilator.

13. A lung ventilator according to claim 10, further including means responsive to source gas pressure and to operation of said trigger mechanism to enable continuous operation of said ventilator upon first application of source gas pressure to said ventilator.

14. A lung ventilator according to claim 10, including means for bypassing said valve arrangement to enable continuous automatic operation of said ventilator.

15. A lung ventilator according to claim 14 in which said bypassing means comprises a stop valve movable between a closed position and an open position biasing means biasing said stop valve towards said open position, gas pressure biasing means connected with said gas pressure source and biasing said stop valve towards its closed position, means for connecting said trigger mechanism with said gas pressure source, whereby said stop valve can be moved to its closed position by operation of said trigger mechanism but can remain in its closed position after release of said trigger mechanism, the arrangement being such that the pressure of said source can balance the force of said biasing means on said stop valve in both the open and closed positions of the stop valve but that upon removal of the source pressure and with said trigger mechanism released, said biasing means can move said stop valve to its open position.

16. A lung ventilator including an outlet branch, said lung ventilator comprising supply connection means for connection with a source of breathable gas under pressure, a patient interface device for application to a patient for communication with the patient's respiratory system, a control system including a trigger mechanism, said control system providing a semi-automatic mode of operation in which, in response to activation of said trigger mechanism, a complete ventilation cycle in accordance with predetermined ventilation parameters is initiated, said control system including means to ensure that said cycle proceeds to completion regardless of any operation or release of said trigger mechanism after the movement which initiated said cycle and before its completion, said ventilator being gas-powered with timing and control functions provided by pneumatic mechanisms, said ventilator comprising a pneumatic oscillator controlled by said trigger mechanism and controlling the supply of gas from said source to said outlet branch.

17. A lung ventilator including an outlet branch, said lung ventilator comprising supply connection means for connection with a source of breathable gas under pressure, a patient interface device for application to a patient for communication with the patient's respiratory system, a control system including a trigger mechanism, said control system providing a semi-automatic mode of operation in which a complete ventilation cycle in accordance with predetermined ventilation parameters may be initiated by manual operation of said trigger mechanism, said cycle proceeding to completion regardless of operation or release of said trigger mechanism after initiation of said cycle and before its completion, said ventilator being gas-powered with timing and control functions provided by pneumatic mechanisms, said ventilator comprising a pneumatic oscillator controlled by said trigger mechanism and controlling the supply of gas from said source to said outlet branch and wherein said oscillator includes an outlet, gas feedback means for gas flow instrumental in maintaining oscillatory behavior of said pneumatic oscillator, valve means controlled by said trigger means incorporated in said gas feedback means for controlling gas flow therethrough, said gas feedback means including a gas flow line incorporating a flow restrictor.

18. A lung ventilator according to claim 17 wherein said pneumatic oscillator comprises a timing chamber, a delivery chamber, a supply connection from such source of gas under pressure to said delivery chamber, a port connecting said delivery chamber with said outlet of the oscillator, a valve member movable between a first position and a second position, said valve member comprising a piston exposed on one side to the gas pressure in said timing chamber and, in said first position, exposed on an opposite side to the gas pressure at said outlet of said oscillator, said valve member in said second position cooperating with a valve seat formed around said port to isolate a part of said delivery chamber in communication with said supply connection means from a part of said delivery chamber in communication with said oscillator output, biasing means such that said valve member will move toward said second position thereof if the pressures in said timing chamber and said delivery chamber are equal, and wherein gas feedback means extends between said delivery chamber and said timing chamber.

19. A lung ventilator including an outlet branch, said lung ventilator comprising a control system providing a semi-automatic mode of operation in which a complete ventilation cycle in accordance with predetermined ventilation parameters may be initiated by operation of a trigger mechanism, said cycle proceeding to completion regardless of operation or release of said trigger mechanism after initiation of said cycle and before its completion, said lung ventilator comprising a pneumatic oscillator and a valve arrangement controlling a flowpath for breathable gas from said oscillator to said outlet branch, said valve arrangement having a controlling trigger mechanism adapted to open said flowpath and being responsive to gas pressure in said outlet branch to maintain said flowpath open while breathable gas is output by said oscillator and in which said valve arrangement comprises an outlet chamber having an inlet port connected to said oscillator, a wall movable to close said inlet port and an outlet port connected to said outlet branch; resilient means acting on said wall to urge said resilient means towards its inlet-port-closing position and said trigger mechanism operable to relieve the action of said resilient means thereby to permit said wall to move to open said inlet port in response to gas pressure thereat, the arrangement being such that gas pressure in said outlet chamber resulting from opening of said inlet port is effective to maintain said wall in an inlet-port-opening position despite the action of said resilient means and wherein said oscillator includes a gas feedback line for gas flow instrumental in maintaining oscillatory behavior of said pneumatic oscillator, said gas feedback line incorporating a flow restrictor, said gas feedback line extending to said pneumatic oscillator from said outlet chamber, whereby oscillatory behavior of said pneumatic oscillator is inhibited as long as said inlet port is closed by said movable wall.

20. A lung ventilator according to claim 19 wherein said pneumatic oscillator comprises a timing chamber, a delivery chamber, a supply connection from a source of gas under pressure to said delivery chamber, said inlet port connecting said delivery chamber with said outlet chamber, a valve member movable between a first position and a second position, said valve member comprising a piston exposed on one side to the gas pressure in said timing chamber and, in said first position, exposed on an opposite side to the gas pressure in said delivery chamber, said valve member in said second position cooperating with a valve seat formed around said inlet port to isolate a part of said delivery chamber in communication with said supply connection from a part of said delivery chamber in communication with said inlet port, biasing means such that said valve member will move toward said second position thereof if the pressures in said timing chamber and said delivery chamber are equal, and wherein said gas feedback line extends between said outlet chamber and said timing chamber.

21. A lung ventilator according to claim 19 including additional biasing means for biasing said wall towards its inlet-port-closing position, said additional biasing means including a biasing member exposed on one side to the pressure in a biasing chamber, whereby an increased gas pressure in said biasing chamber produces an increased force biasing said wall towards its inlet-port-closing position, bias pressure line extending to said biasing chamber, means connecting said bias pressure line with said outlet chamber check valve means in said bias pressure line oriented to permit gas flow therethrough only in the direction towards said biasing chamber, a pilot line in communication with said bias pressure line between said check valve means and said biasing chamber, said pilot line extending to a pilot valve comprising a release orifice, a valve seat around said release orifice, a valve member cooperating with said release orifice and connected with said trigger mechanism, whereby release of said trigger mechanism, with consequent release of gas pressure from said biasing chamber, is necessary to reduce the biasing force on said wall sufficiently for the pressure within said delivery chamber to move said wall from its said inlet-port-closing position, at the beginning of a ventilation cycle.

22. A lung ventilator according to claim 19, including latching means for holding said trigger mechanism in a position to relieve the action of said resilient means and thereby to enable continuous automatic operation of said ventilator.

23. A lung ventilator according to claim 22 wherein said latching means includes a manually operable member movable between a latching position and a released position, said ventilator comprising a by-pass line connected across said flow restrictor for by-passing said by-pass line, said by-pass line including a check valve and a stop valve in series, said check valve being oriented to prevent gas flow therethrough in the direction towards said timing chamber and means coupling said stop valve with said latching means such that said stop valve is necessarily closed when said latching means is in its position to enable continuous automatic operation of said ventilator and is open when said latching means is in its released position.

* * * * *